United States Patent [19]
Stangerup

[11] Patent Number: 5,431,636
[45] Date of Patent: Jul. 11, 1995

[54] DEVICE FOR EQUALIZING PRESSURE IN THE MIDDLE EAR

[75] Inventor: Sven-Erik Stangerup, Hilleröd, Denmark

[73] Assignee: Abigo Medical AB, Askim, Sweden

[21] Appl. No.: 138,386

[22] Filed: Oct. 20, 1993

Related U.S. Application Data

[63] Continuation of Ser. No. 850,849, Mar. 13, 1992, abandoned.

[30] Foreign Application Priority Data

Mar. 15, 1991 [SE] Sweden .................................. 9100791

[51] Int. Cl.⁶ .............................................. A61B 5/08
[52] U.S. Cl. ................................... 604/215; 128/728
[58] Field of Search ............... 128/728, 730, 746, 766; 604/215, 212–214

[56] References Cited

U.S. PATENT DOCUMENTS

| | | | |
|---|---|---|---|
| 3,426,745 | 2/1969 | Farr | 128/728 |
| 4,291,704 | 9/1981 | Petty et al. | 128/728 |
| 4,327,741 | 5/1982 | Watson et al. | 128/728 |
| 4,817,626 | 4/1989 | Blaine | 128/728 |

Primary Examiner—C. Fred Rosenbaum
Assistant Examiner—Manuel Mendez
Attorney, Agent, or Firm—Burns, Doane, Swecker & Mathis

[57] ABSTRACT

A device for equalizing the pressure in the middle ear is comprised of a unit having one end that is to be positioned in a nostril and an opposite end that is provided with a rib. A balloon is positioned on the unit adjacent the rib. The unit is provided with a through hole whose smallest cross-sectional area is greater than or equal to 7 mm². The elasticity of the balloon is such that a counter pressure of at least 20 mBar is produced upon being blown up.

4 Claims, 1 Drawing Sheet

DEVICE FOR EQUALIZING PRESSURE IN THE MIDDLE EAR

This application is a continuation of application Ser. No. 07/850,849, filed Mar. 13, 1992 now abandoned.

DESCRIPTION

1. Technical Field

The present invention relates to a device for obtaining an equalization of the pressure in the middle ear, comprising a unit adapted to be positioned in a nostril and comprising one end for being positioned in the nostril and an opposite end provided with a rib on which end a balloon is arranged.

The object of the present invention is to obtain a device for pressure equalization in the middle ear in order to reduce negative pressure and liquid formation in the middle ear.

2. Background of the Invention

Many people and in particular children suffer from a dysfunction of the Eustachian tube, which leads to negative pressure and formation of liquid in the middle ear causing great disability to those suffering therefrom. After a short time of negative pressure the number of mucous producing glands increases in the middle ear causing production of liquid as a consequence. In addition to reduced hearing ability, acute otitis media readily results.

For treating secretary otitis media different methods have hitherto been used, viz prolonged antibiotic treatment, adenoid ectonomi, paracentesis, politerization, and most effective of all, introduction of a venting tube in the tympanic membrane. The latter method is carried out most often during total anaesthetization. Due to a pressing out of the tube this surgical incision may be carried out a number of times. This leads in turn to a number of complications such as development of changes of the tympanic membrane, and a permanent perforation of the tympanic membrane.

Most adults can equalize any negative pressure present in the middle ear using the "Valsalva's manoeuvre", i.e. by pressing the nostrils together, closing the mouth and by means of the diaphragm pressure and increasing the pressure of the air in the mouth and nose cavity. The increased pressure so created is transplanted through the Eustachian tube and equalized the negative pressure in the middle ear.

Many children, however, can not learn this technique.

Thus, demands have been raised for a device to eliminate this problem and to equalize the negative pressure in the middle ear of persons that can not handle the Valsalva's manoeuvre, to facilitate the learning of the Valsalva's manoeuvre, to control an over pressure in the mouth and nose cavity during exercise of the manoeuvre and to function as a control of the function of the Eustachian tube in patients, pilots and divers.

SUMMARY OF THE PRESENT INVENTION

It has now been shown possible to be able to solve this problem by means of the present invention in which that the unit is provided with a through-going hole having a smallest cross section area not exceeding 7 mm$^2$ and whereby the balloon upon being blown up, provides a counter pressure of at least 20 mBar.

BRIEF DESCRIPTION OF THE DRAWING FIGURES

The invention will be described more in detail in the following with reference to the attached drawing figures wherein FIG. 1 shows a device according to the present invention seen in a longitudinal cross-section, and FIG. 2 shows a further embodiment of the invention seen in a longitudinal cross-section.

DETAILED DESCRIPTION OF THE INVENTION

Figure 1:
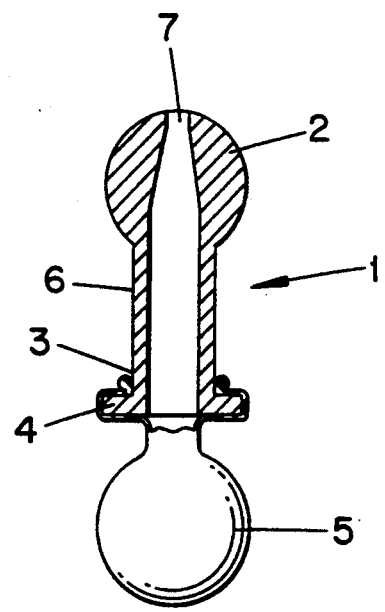
Figure 2:
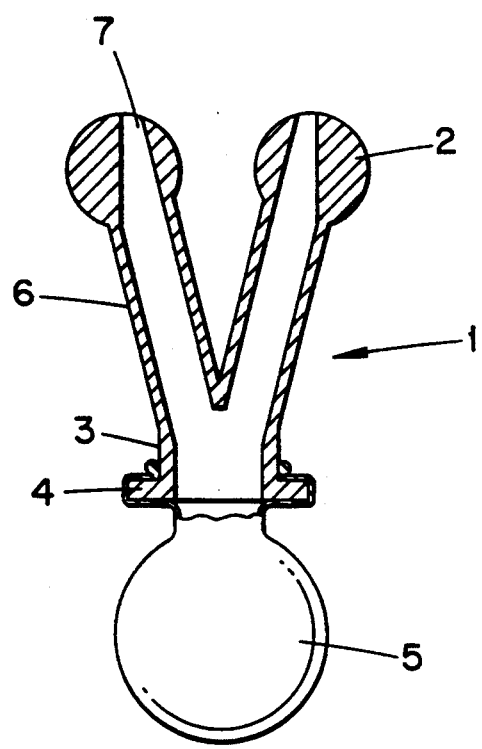

The device comprises a unit 1 provided with a tube, the one end 2 of said unit being adapted to be introduced into a nostril to thereby close against the same. The other end 3 of the unit 1 is provided with a rib 4. A balloon 5 is arranged over this rib 4. The intermediate part 6 of the unit constitutes a handle. Through the unit 1 a bore 7 extends, which may have a varied cross-sectional area.

The device functions so that the end 2 is introduced into one of the nostrils whereafter the patient closes the other nostril, closes his/her mouth and blows the balloon by means of diaphragmatic pressure by blowing air through the bone 7 and into the balloon. Then the patient, still with the unit against the nostril the second nostril closed and the mouth shut, carries out a swallowing movement or a bowing. turning of the head, whereby a muscle contraction leads to the Eustachian tube being widened so that the increased pressure present in the mouth and nose cavity is transplanted through said Eustachian tube and equalizes the negative pressure present in the middle ear. In some cases this occurs already during the blowing up phase.

In order to facilitate handing, the unit can be designed to have two ends 2 to be introduced in both nostrils, whereby one end can be closed; or both ends can be provided with a through-going hole 7 for blowing up the balloon. In the latter case the holes have a smaller cross-sectional area than if only one through-going hole exists. The through-going hole 7 may have any possible form but is preferably cylindrical or cylindrical and provided with a venturi.

It has turned out that the elasticity of the balloon is of great importance for the final increased pressure and thereby for the final result. Thus it should have an elasticity which gives a smallest blowing up resistance of 20 mBar in order to achieve a therapeutic effect, whereby the counter pressure preferably is 40 to 60 mBar. The cross-sectional area at a single through-going hole 7 should be 7 to 30 mm$^2$. If a double through-going hole 7 is used the smallest cross-sectional area should not be below 7 mm$^2$.

At tests using a unit comprising an opening having a diameter of 4 mm and a suitable balloon the following blowing up pressures have been achieved at 20° C. and a flow of 2 1/min during 30 seconds. The maximum pressure obtained was registered according to the following Table 1.

TABLE 1

| Number of blowing-ups | Mean pressure mBar | Range mBar |
| --- | --- | --- |
| 1 | 60.0 | 57–63 |
| 2 | 48.6 | 46–52 |
| 3 | 45.8 | 44–48 |
| 4 | 44.2 | 42–47 |
| 5 | 43.2 | 41–47 |

TABLE 1-continued

| Number of blowing-ups | Mean pressure mBar | Range mBar |
|---|---|---|
| 6 | 42.6 | 41–45 |
| 7 | 41.8 | 40–44 |
| 8 | 41.4 | 39–43 |
| 9 | 40.6 | 38–42 |
| 10 | 39.6 | 38–41 |

The maximum blowing out pressure of the balloon was determined as well and the results are given in Table 2 below.

TABLE 2

| Number of blowing-ups | Mean pressure mBar | Range mBar |
|---|---|---|
| 1 | 31.2 | 28–34 |
| 2 | 28.0 | 26–30 |
| 3 | 26.8 | 25–29 |
| 4 | 26.4 | 25–28 |
| 5 | 26.0 | 24–28 |
| 6 | 25.8 | 24–28 |
| 7 | 25.6 | 24–27 |
| 8 | 25.4 | 24–27 |
| 9 | 25.4 | 24–27 |
| 10 | 25.0 | 24–26 |

The emptying rate at different hole diameters was determined as well. Hereby the balloon was filled with 2 l of atmospheric air. The results obtained are given in Table 3 below.

TABLE 3

| Hole diameter mm | Emptying rate sec. |
|---|---|
| 1 | 64.5 |
| 2 | 13.5 |
| 3 | 9.0 |
| 4 | 4.0 |
| 5 | 3.2 |
| 6 | 3.0 |
| 7 | 2.9 |
| 8 | 2.9 |

The balloon used should have such an elasticity such that it can be used at least about 10 times before exchange.

Tests carried out using a control group have turned out to improve the tympanometric conditions in 64% of the cases, that 34% were unchanged, and that 2% had deteriorated using the present device, while in the control group the tympanometry had improved in 15% of the cases, 71% were unchanged and 14% of the cases had deteriorated. The device thus leads to an undoubtful clinical effect.

Further, it has turned out to be of importance to be able to let the air pass back in through the nose cavity during a continued closing of the mouth and carrying out of one or more consecutive swallowing movements. Hereby the hole diameter of the boring is of great importance for the final effect as the emptying of the balloon should be carried out during such a time period that the patient is enforced to swallow and thereby to enlarge the Eustachian tube.

The device might also be provided with an opening on the intermediate part 6 of the unit to be connected to a venturi tube and drug containing ampoule or bottle for the addition of a therapeutic agent when the air is allowed to flow back into the nose cavity. Thereby the patient's own expiration air will serve as a driving medium for e.g. a mucous membrane decongestant agent or an antiallergic agent.

I claim:

1. Device for equalizing the pressure in the middle ear, comprising a unit having a first end for being positioned in a nostril and an oppositely positioned second end that is provided with a rib, and a balloon mounted on the unit at the second end, said unit including an intermediate part positioned between said first and second ends, said intermediate part having an opening for connection to a venturi tube to permit the addition of a therapeutic agent upon return of air from the balloon to a nose cavity, said unit having a through hole extending therethrough whose smallest cross-sectional area is greater than or equal to 7 $mm^2$, said balloon possessing an elasticity that produces a counter pressure of at least 20 mBar upon being blown up.

2. Device according to claim 1, wherein said balloon possesses an elasticity that produces a counter pressure of 40 mBar to 60 mBar upon being blown up.

3. Device according to claim 1, wherein the smallest cross-sectional area of said through hole is between 7 $mm^2$ and 30 $mm^2$.

4. Device according to claim 1, wherein said unit includes two first ends for being individually positioned in a nostril.

* * * * *